(12) United States Patent
Salvetzki

(10) Patent No.: US 8,323,938 B2
(45) Date of Patent: Dec. 4, 2012

(54) PROCESS FOR THE BIOLOGICAL GENERATION OF METHANE

(75) Inventor: Ralf Salvetzki, Wennigsen (DE)

(73) Assignee: Ralf Salvetzki, Wennigsen (DE)

( * ) Notice: Subject to any disclaimer, the term of this patent is extended or adjusted under 35 U.S.C. 154(b) by 481 days.

(21) Appl. No.: 12/518,407

(22) PCT Filed: Dec. 11, 2007

(86) PCT No.: PCT/DE2007/002234
§ 371 (c)(1),
(2), (4) Date: Oct. 26, 2009

(87) PCT Pub. No.: WO2008/071175
PCT Pub. Date: Jun. 19, 2008

(65) Prior Publication Data
US 2010/0099157 A1    Apr. 22, 2010

(30) Foreign Application Priority Data

Dec. 11, 2006 (DE) .......... 10 2006 058 599
Jan. 8, 2007 (DE) .......... 10 2007 002 009
Jun. 20, 2007 (DE) .......... 10 2007 028 879
Jul. 6, 2007 (DE) .......... 10 2007 031 688

(51) Int. Cl.
*C12P 5/02* (2006.01)

(52) U.S. Cl. ...................................... 435/167

(58) Field of Classification Search .......... 435/167
See application file for complete search history.

(56) References Cited

U.S. PATENT DOCUMENTS

| | | |
|---|---|---|
| 4,148,690 A | 4/1979 | Weetall |
| 4,476,105 A | 10/1984 | Greenbaum |
| 4,532,210 A | 7/1985 | Miura et al. |
| 4,609,383 A | 9/1986 | Bonaventura et al. |
| 6,391,256 B1 | 5/2002 | Moon et al. |
| 2001/0053543 A1 | 12/2001 | Anastasios et al. |

FOREIGN PATENT DOCUMENTS

| | | |
|---|---|---|
| AU | 2004229070 | 6/2005 |
| DE | 297 450 | 1/1992 |
| EP | 1 264 895 | 12/2002 |
| EP | 1 574 581 | 9/2005 |
| FR | 2 537 992 | 6/1984 |
| JP | 58-060992 A | 4/1983 |
| JP | 58-76094 | 5/1983 |
| JP | 61-081796 A | 4/1986 |
| JP | 61-69783 A | 6/1994 |
| JP | 10-066996 A | 3/1998 |
| JP | 2005-073519 A | 3/2005 |
| WO | WO 91/02701 | 3/1991 |
| WO | WO 03/013748 | 2/2003 |
| WO | WO 2005/003024 A1 | 1/2005 |

OTHER PUBLICATIONS

Addison M. Rosenkrans and Alvin I. Krasna; *Stimulation of Hydrogen Photoproduction in Algae by Removal of Oxygen by Reagents that Combine Reversibly with Oxygen*; Biotechnology and Bioengineering; 1984; pp. 1334-1342; vol. XXVI; John Wiley & Sons, Inc.

Addison M. Rosenkrans and Alvin I. Krasna; *Effect of Oxygen Removal on Hydrogen Photo Production in Algae*; Biotechnology and Bioengineering; 1984; pp. 1897-1904; vol. 25, Issue 7; John Wiley & Sons, Inc. (Abstract Only).

Rosendrans, Addison M.; Krasna, Alvin; "Stimulation of Hydrogen Photoproduction in Algae by Removal of Oxygen by Reagents that Combine Reversibly with Oxygen"; Biotechnology and Bioengineering, vol. XXVI, pp. 1334-1342 (1984).

International Preliminary Report on Patentability and Written Opinion of the International Searching Authority for International Application No. PCT/DE2007/002234, (Jul. 2007).

*Primary Examiner* — Chih-Min Kam
(74) *Attorney, Agent, or Firm* — Alston & Bird LLP

(57) ABSTRACT

A process is specified for the biological generation of methane ($CH_4$), which process is firstly environmentally friendly and inexpensive, and secondly avoids the use of fossil deposits. The process is divided into two steps, wherein first hydrogen ($H_2$) and oxygen ($O_2$) are generated from carbon dioxide ($CO_2$) and water ($H_2O$) by algae with the action of light. In the second step, methane ($CH_4$) is isolated by methanogenesis bacteria from the hydrogen ($H_2$) which is generated and from carbon dioxide ($CO_2$). To increase the yield of the process, interfering intracellular oxygen ($O_2$) can be bound in the algae and/or in the methanogenesis bacteria.

23 Claims, 5 Drawing Sheets

PROCESS FOR THE BIOLOGICAL GENERATION OF METHANE

CROSS-REFERENCE TO RELATED APPLICATIONS

The present application is a national stage entry of PCT/DE07/02234, filed Dec. 11, 2007, and which is hereby incorporated herein in its entirety by reference.

BACKGROUND OF THE INVENTION

1. Field of the Invention

The present invention concerns a process for biological generation of methane.

2. Description of Related Art

Methane is an important energy carrier and a significant starting substance for the chemical industry. Methane is mostly produced from natural gas, of which it is the main component. For this purpose, fossil deposits in which natural gas and petroleum generally occur together are exploited. Such deposits are found, for example, in Russia, or also beneath the sea, for example, in the North Sea.

The availability of such fossil natural gas deposits, however, is limited. In addition, economic dependence on natural gas-producing countries can occur. Moreover, methane is present in natural gas, in addition to a number of other components, and must be separated from the secondary components by costly methods in order to obtain pure methane.

The main problem in using methane from fossil deposits, however, is the strong greenhouse potential that methane has, in the first place. In the production and transport of methane occurring as fossil fuel, a significant loss of the gas unavoidably occurs, and this fraction reaches the atmosphere as a greenhouse gas.

On the other hand, use (i.e., combustion) of fossil methane intensifies the greenhouse effect in that additional carbon dioxide reaches the atmosphere and can act accordingly as a greenhouse gas.

It is also known to recover methane-containing gases from biomass (so-called biogas process). A biogas installation for production of methane-containing gases is known from DE 10 2004 035 997 A1. Biogas generation, however, has the drawback that only very impure methane is produced, which is contaminated by carbon dioxide, water vapor, ammonia, hydrogen sulfide and other components. Moreover, sufficient biomass is not available to be able to ultimately replace fossil deposits.

Finally, it is known that several billion tons of methane in the form of methane hydrate are found on the bottom of the Earth's seas. Production of these deposits, however, is still not commercially possible and only appears to be attainable with significant cost.

The task underlying the present invention is therefore to provide an environmentally safe and cost-effective method for generation of methane that dispenses with utilization of fossil deposits.

SUMMARY OF VARIOUS EMBODIMENTS

The aforementioned task is solved according to the invention with the features of claim 1. The method according to the invention for biological generation of methane has the following steps:

Generation of hydrogen ($H_2$) and oxygen ($O_2$) from carbon dioxide ($CO_2$) and water ($H_2O$) by algae under the influence of light (hydrogenesis), Separation of the produced oxygen ($O_2$) from the generated hydrogen ($H_2$), Generation of methane ($CH_4$) from the produced hydrogen ($H_2$) and carbon dioxide ($CO_2$) by methanogenic bacteria (methanogenesis), Separation and optional liquefaction of the generated methane ($CH_4$).

Advantageous embodiments of the process according to the invention can be deduced from the subordinate claims.

It was recognized according to the invention that preparation of methane can be divided into two steps, in which an environmentally neutral bioreaction can occur in both steps.

Thus, hydrogen and oxygen are initially produced from carbon dioxide and water by using appropriate algae.

The employed carbon dioxide can be obtained from the surrounding atmosphere, for example, by air liquefaction methods with subsequent dry ice formation. The percentage of greenhouse-active carbon dioxide in the atmosphere is reduced on this account. Carbon dioxide from industrial or combustion processes can also be used, so that the carbon dioxide load on the atmosphere is directly reduced.

The oxygen generated in this first step by algae is separated and can be fed to other applications. The hydrogen generated in the first step remains.

According to the invention, methane is now generated in the second step from the generated hydrogen and additional carbon dioxide by using appropriate methanogenic bacteria. Additional carbon dioxide is then consumed.

Finally, the generated methane can be separated from the remaining educts hydrogen and carbon dioxide, and optionally liquefied.

By consuming carbon dioxide during methane production according to the invention, a process that is carbon dioxide-neutral overall is provided. This means that the generated methane, during thermal conversion, produces no additional greenhouse-damaging carbon dioxide, since the corresponding amount of carbon dioxide was already taken from the atmosphere during production. Sunlight can then be used as energy carrier, which further improves the energy balance of the process. The proposed process can therefore become an alternative to the environmentally safe energy sources wind energy and solar energy.

Consequently, an environmentally safe and cost-effective process for production of methane is provided, which dispenses with utilization of fossil deposits.

In a first variant of the invention, the algae used to generate hydrogen are prepared in aqueous solution. Appropriate nutrients are added to this solution periodically or continuously. The employed algae are furnished an optimal environment on this account and it becomes possible to operate the process according to the invention without undesired interruptions.

The algae used to generate hydrogen can be green algae, especially *Chlamydomonas reinhardtii*. These algae are particularly suited for hydrogen production and are optimally in harmony with the other steps of the process according to the invention.

In a modification of the process, the algae used for generation of hydrogen are separated from the light source, especially sunlight, by an essentially transparent disk. Because of this, the employed algae can utilize sunlight as an energy carrier without being directly exposed to the environment.

A disk is then preferably used, which has a self-cleaning effect (lotus effect) on the side facing away from the light. This effect can be produced by a silane coating. Use of such a disk ensures that no algae grow on the inside of the disk or no soiling adheres, which might prevent penetration of light to the inside of the disk.

It was also recognized according to the invention that oxygen interferes intracellularly with the hydrogenesis step. A process is therefore proposed, in which the intracellular oxygen is at least partially bonded, preferably already during the hydrogenesis step. This prevents oxygen from being enriched in the cells of the employed algae and thus inhibiting hydrogen production.

It was also recognized by the present inventor that, in addition to unduly high intracellular oxygen content, an unduly high light radiation (more than about 2000 W/m$^2$) also leads to formation of oxygen radicals and, in so doing, also inhibits hydrogenesis. To compensate for this effect, the content of intracellular oxygen can be reduced with the proposed process, in order to compensate for this undesired effect. It should then be emphasized that the term "intracellular oxygen" subsequently also includes oxygen radicals present intracellularly, which also inhibit hydrogenesis.

The intracellular oxygen can be bonded during or after the hydrogenesis step. In other words, the intracellular oxygen can be continuously trapped already during formation. This has advantages with reference to uniform reaction conditions. On the other hand, the intracellular oxygen can be bonded from time to time, or also only during the dark phase of hydrogenesis (especially at night). In this procedure, no interference or interruption of hydrogen production occurs.

It was also recognized that intracellular oxygen also inhibits methanogenesis in the methanogenic bacteria. For this reason, a preferred variant of the process is also proposed below, in which the intracellular oxygen of the methanogenic bacteria is also bonded. The subsequently proposed advantageous variants for the bonding of intracellular oxygen with reference to algae are therefore not explicitly restricted to the hydrogenesis step. Instead these modifications are also advantageously suited for bonding of intracellular oxygen of the methanogenic bacteria, and are also proposed in this respect as embodiments of the process according to the invention.

A variant is preferred, in which the intracellular oxygen is bonded by adding at least one binder.

It is then preferred that the binder or binders is or are regenerated after absorption of oxygen. In the most favorable case, the binder can remain in the cell and become active again there on this account. In addition, a cost-effective and environmentally safe method is implemented.

The intracellular oxygen can be bonded biochemically.

In this context, a method is initially proposed, in which myoglobin is added as binder. Biochemically produced myoglobin can be introduced to the hydrogenesis bioreactor. Penetration of myoglobin into the algae cells can be favored by the fact that the membranes of the algae are opened by electroporation. During electroporation, the cells are exposed briefly to strong electric fields, so that the plasma membranes temporarily become permeable. Myoglobin can penetrate particularly simply into the cells on this account and bind the intracellular oxygen. In another embodiment, the myoglobin is introduced by genetic engineering into the genome of the algae by means of a DNA transcription technique, so that the myoglobin can be produced in the future by the cell itself.

In a modification of the process, porphorin is added as binder. Porphorin-iron complexes are then preferably introduced to the hydrogenesis bioreactor. The porphorins can then be sterically hindered, so that the oxygen absorption prevents reduction of iron. The penetration of the binder into the algae cell can also be favored by electroporation.

With reference to the aforementioned modifications of the process, an embodiment is preferred, in which myoglobin and/or porphorin, after absorption of oxygen, is or are regenerated electrochemically and/or biochemically and/or physically. Initially, the myglobin or the porphorin-iron complexes can be reduced by electrochemical reduction to iron ion ($Fe^{2+}$) complexes. This electrochemical reduction can preferably be conducted during the dark phase (at night). Myglobin and porphorin-iron complexes can also be reduced by biochemical reduction with the enzyme NADPH to the already mentioned iron ion complexes.

Finally, myoglobin can preferably be physically regenerated during the dark phase (at night), in which it is exposed to carbon dioxide. The carbon dioxide molecules displace the oxygen molecules from myoglobin and assume their positions when sufficiently high partial pressure is present.

In another preferred variant of the process according to the invention, the intracellular oxygen is chemically bonded.

It is then initially preferred that hydrazine and/or a hydrazine salt, especially iron hydrazine, is added as binder. The hydrazine is directly introduced to the hydrogenesis bioreactor. The hydrazine or its salts cause a reducing effect, so that intracellular oxygen or oxygen radicals are bonded.

Another possibility for chemical bonding of intracellular oxygen consists of adding a terpene, especially α-terpene and/or isoprene and/or a derivative, as binder. Terpenes generally have a reducing effect, so that intracellular oxygen or oxygen radicals are bonded. With particular preference, the triphenylmethane dye eosin and/or a heme protein of the cytochrome P450 family is added to the terpene. These substances, as so-called photosensitizers, reinforce the reducing effect of terpene.

If hydrogenesis occurs in an aqueous algal medium, a variant is generally preferred, in which the gaseous intermediate products hydrogen and oxygen of the first step are initially separated from the algal medium before the gas mixture hydrogen and oxygen is separated. In a preferred variant, the gaseous intermediate products hydrogen and oxygen are separated from the algal medium by a membrane, especially a porous membrane made of CLPE (crosslinked polyethylene). The gaseous intermediate products can then diffuse through the membrane, while the generally aqueous algal medium is prevented from passing through the membrane. It is then found that the mentioned membrane made of CLPE is particularly suited for preparation of the mixture partners that are present.

In a modification of this variant, the membrane is fixed on both sides in hexagonally closest spherical packing. Particularly reliable fixation of the membrane is achieved on this account.

In another variant, a CLPE membrane with an inner layer of PATBS (polyacrylamide tert-butyl-sulfonic acid) is used. The inner layer of PATBS further increases the performance of the proposed CLPE membrane in advantageous fashion for separation of the mixture partners.

In this context, a modification of the process is preferred, in which a multilayer membrane is used, whose layers are joined to each other, at least in areas, especially in a circular or honeycomb pattern. By joining of the different layers of the membrane, an increased pressure resistance is provided, so that the gas pressure can be advantageously increased.

In another embodiment, a black membrane is used in the hydrogenesis step. The black membrane absorbs most of the introduced light, so that heating of the membrane and the surrounding algal medium is achieved. Diffusion of both oxygen and hydrogen is favored by heat development. In addition, the heat energy can be taken off and utilized in other ways, for example, by a heat exchanger. It is also possible to connect the black membrane directly to a heat transfer device, so that the introduced heat energy can be directly taken off.

Since the carbon dioxide is converted by the employed algae, passage of carbon dioxide to the gas side of the membrane (i.e., in the direction of the gaseous mixture of hydrogen and oxygen) is undesired. The osmotic pressure of carbon dioxide in the gas side of the membrane can therefore be increased, so that a desired minimum concentration of carbon dioxide is maintained in the algal medium.

The gaseous mixture partners oxygen and hydrogen produced in the first step are separated from each other, preferably by gas liquefaction, especially according to the Linde method. The Linde method is known per se. A gas or gas mixture is then cooled until the individual mixture partners reach their boiling point and appear as liquid. In this case, the boiling point of oxygen lies about 70 kelvin above the boiling point of hydrogen, so that oxygen becomes liquid first. Use of a gas liquefaction method is particularly advantageous, if very pure components are to be recovered.

Ultrapure fresh water can be obtained as byproduct of the process from pure oxygen and pure hydrogen, especially using waste heat from the hydrogenesis step.

A variant of the invention is preferred overall, in which the methanogenic bacteria used for generation of methane are also furnished in an aqueous solution. Appropriate nutrients can also be fed periodically or continuously to this solution. An optimal environment is therefore provided for the employed methanogenic bacteria. In addition, uninterrupted performance of the process according to the invention is made possible.

In another variant, the methanogenic bacteria used to generate methane are one or a mixture of the species *Methanobacterium thermoautotropicum, Methanobacillus, Methanobacterium, Methanococcus, Methanosarcina* and *Methanothrix*. It was found that the mentioned bacteria harmonize particularly well with the other steps of the process according to the invention.

In the second step of the process, the hydrogen and carbon dioxide can be fed to the methanogenic bacteria under anaerobic conditions and/or at a temperature of about 60° C. The mentioned conditions have proven optimal, in order to provide the highest possible methane yield in conjunction with a long lifetime and particularly uniform activity of the employed bacteria.

It was also recognized that intracellular oxygen or intracellular oxygen radicals not only inhibit hydrogen production of the algae, but also reduce productivity of the methanogenic bacteria. A particularly preferred modification of the process according to the invention therefore consists of also reducing the content of intracellular oxygen within the methanogenic bacteria. For this purpose, all measures that were discussed as preferred variants for reduction of intracellular oxygen within the algae of the hydrogenesis step are explicitly proposed. In other words, all of these measures are also advantageously suitable for use on the methanogenic bacteria, but are not mentioned in detail again, to avoid repetitions.

A variant is preferred, in which separation of methane from the bacterial medium occurs via a membrane, especially a porous membrane made of CLPE (crosslinked polyethylene).

The membrane of the second step can also be fixed in a hexagonally closest spherical packing.

Use of a membrane having an inner layer of PATBS is then preferred.

Here again, a multilayer membrane can advantageously be used, whose layers are joined to each other, at least in areas, especially in a circular or honeycomb pattern.

With reference to the last-named variants, to avoid repetitions, the variants with reference to advantageous features of the membrane used in the first step are referred to.

Also with reference to the second reaction step, a modification of the process according to the invention is proposed, in which the osmotic pressure of the carbon dioxide is increased on the gas side of the membrane. A uniformly high concentration of carbon dioxide in the bacterial medium can be ensured on this account. This is advantageous, since the carbon dioxide is ultimately converted by the bacteria to methane.

An embodiment of the process according to the invention is also proposed, in which separation of the methane generated in the second step from the hydrogen occurs by gas liquefaction, especially according to the Linde method. With reference to the advantages of this variant, the explanations relative to separation of oxygen and hydrogen can be referred to.

With reference to both steps of the process according to the invention, in which carbon dioxide is consumed, it is proposed that the carbon dioxide fed to the algae and/or the methanogenic bacteria is produced from dry ice, in which the dry ice is optionally produced from air liquefaction, especially according to the Linde method. Carbon dioxide or dry ice can then be provided, which contains virtually no contaminants. In addition, carbon dioxide is removed from the surrounding air, which has an advantageous effect on the greenhouse effect.

As an alternative or in addition, carbon dioxide fed to the algae and/or methanogenic bacteria can be furnished from carbon dioxide-rich gas streams, especially from industrial and combustion processes. This modification of the process is especially advantageous with respect to improvement of the carbon dioxide balance of waste incinerators and power plants. Thus, from actually environmentally damaging waste gas streams, methane can be produced with the present process, which can be used as a starting material for the chemical industry or for carbon dioxide-neutral combustion.

With respect to improvement of the energy balance and reduction in emission of greenhouse-active carbon dioxide, a modification of the process is proposed, in which unconsumed or unconverted carbon dioxide is recovered and returned to the process, especially by a cooling trap.

Finally, with respect to an additionally improved methane yield of the process, an embodiment is preferred, in which the excess algae and/or bacterial material that forms is periodically or continuously removed from the process and fed to a biogas process for additional methane production. During performance of the method according to the invention, biomass is continuously produced, which must be removed from time to time or continuously, because of the fixed installation sites. In this modification of the process, this biomass, which otherwise would have to be disposed of (possibly with additional subsequent cost), can be fed to another useful application.

In the sense of optimized energy balance of the process according to the invention, heat can be taken off from the hydrogenesis step, especially by a heat exchanger or heat pump. To obtain a particularly large amount of heat, as already mentioned, a black membrane can be used in the hydrogenesis step. The excess heat can be usefully reused or transferred within the process.

Heat can then be transferred between the hydrogenesis step and the methanogenesis step. In other words, waste heat from the hydrogenesis step can be advantageously used for methanogenesis. However, since methanogenesis generally occurs at a much higher temperature level than hydrogenesis, use of a heat pump is the thing to do here.

BRIEF DESCRIPTION OF THE SEVERAL VIEWS OF THE DRAWINGS

There are now different possibilities for configuring and modifying the teachings of the present invention advantageously. For this purpose, on the one hand, the subordinate claims and, on the other hand, the subsequent explanation of a preferred practical example of the process according to the invention with reference to the drawing are referred to. In conjunction with explanation of the preferred practical example with reference to the drawing, generally preferred embodiments and modifications of the teachings are also explained. In the drawing

DETAILED DESCRIPTION

Figure 1:
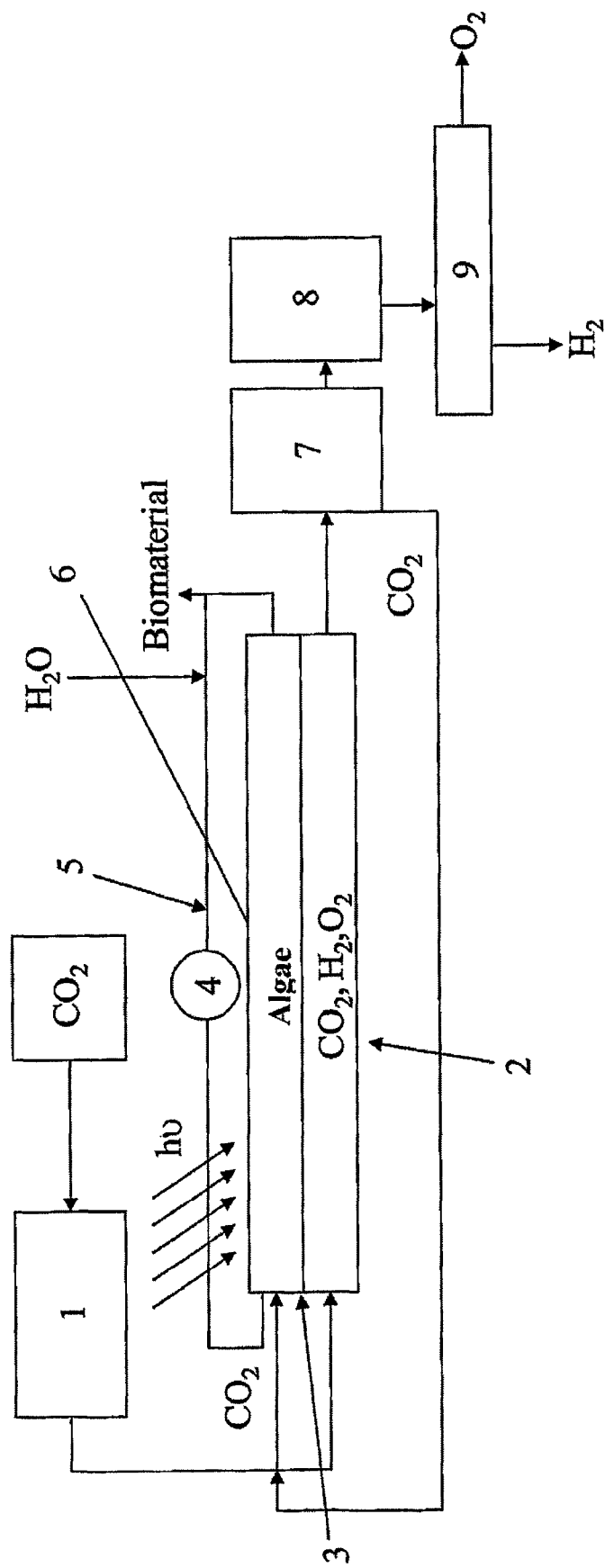
FIG. 1 shows a schematic view of the partial step of the variant of the process according to the invention, in which hydrogen and oxygen are generated.

FIG. 1 shows a schematic view of part of the proposed variant of the overall process. This first part pertains to generation of hydrogen and oxygen by algae and separation of the produced oxygen from hydrogen.

At the beginning of the process, carbon dioxide ($CO_2$) is supplied. This carbon dioxide can be supplied, for example, from gas liquefaction according to the Linde method. The carbon dioxide can also be directly taken from gas liquefaction as dry ice. As an alternative, gaseous carbon dioxide ($CO_2$) can be converted to dry ice in a dry ice generator 1.

The carbon dioxide ($CO_2$) is introduced to a bioreactor 2. An aqueous solution of green algae (*Chlamydomonas reinhardtii*) is present in this bioreactor. The aqueous green algae solution is separated from the gas space of the bioreactor 2 by a membrane 3 made of CLPE. The furnished carbon dioxide is introduced to the aqueous algae solution and always circulated with a pump 4.

In addition, nutrients 5, as well as water ($H_2O$), are continuously fed to the aqueous solution of green algae.

The algae are separated from the environment by an essentially transparent disk 6. Because of radiation or light (hv), especially sunlight, and through supply of the algae with nutrients, water and carbon dioxide, the employed green algae produce hydrogen ($H_2$) and oxygen ($O_2$). These intermediates can be transferred through membrane 3 into the gas space of the bioreactor 2 and withdrawn.

To increase the osmotic pressure of carbon dioxide ($CO_2$) on the gas side of membrane 3, carbon dioxide ($CO_2$) is also fed to the gas space of bioreactor 2.

In also advantageous fashion, intracellular oxygen and oxygen radicals can be bonded in the algae. For this purpose, a binder can be added to bioreactor 2. Appropriate binders include myoglobin, porphorin, hydrazine or terpenes. Such binders can penetrate the algae cells and bind the intracellular oxygen there. Penetration of the binder into the cell can be facilitated by electroporation. In this case, electrodes are mounted within the bioreactor 2, which are not shown here.

The employed binders can be regenerated in different ways, for which purpose the previous comments are referred to. If the binder or binders are regenerated electrochemically, electrodes are also arranged in the bioreactor 2, which are not shown here. The same electrodes can optionally be used for the electroporation and the electrochemical regeneration.

Carbon dioxide ($CO_2$) emerging from the bioreactor 2 with the intermediate products hydrogen ($H_2$) and oxygen ($O_2$) is separated in a cooling trap 7 and returned to circulation.

Separation of the intermediates oxygen ($O_2$) and hydrogen ($H_2$) occurs via a gas liquefaction 8 and fractionation 9.

Because of continuous growth of algae in bioreactor 2, excess biomaterial can be continuously or periodically removed from it. This biomaterial is used for further methane production in a biogas method.

Excess heat can be continuously removed from bioreactor 2. For this purpose, a heat exchanger (not shown) is preferably used. In addition, with respect to improved energy balance, heat can be diverted from the bioreactor 2 by means of a heat pump (not shown) and fed to the bioreactor 2' for methanogenesis (see FIG. 2) at a higher temperature level.

Figure 2:
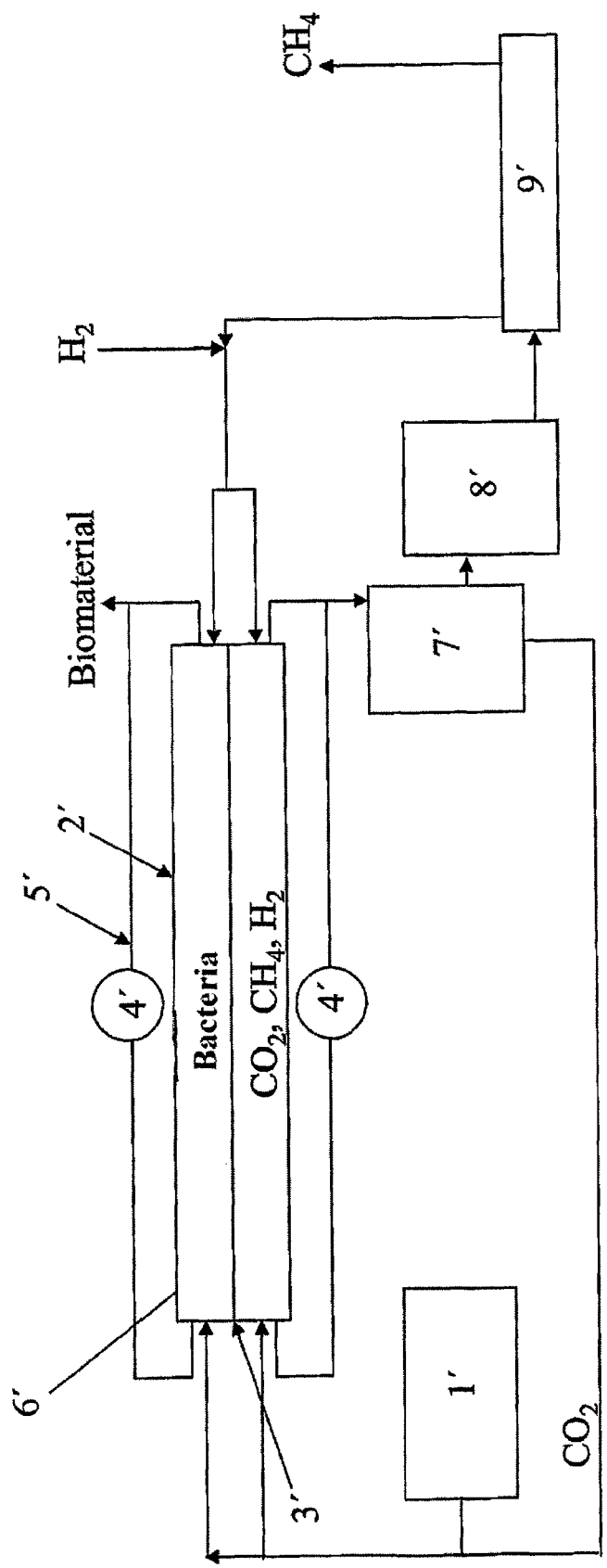
FIG. 2 shows a schematic view of the partial step of the variant of the process according to the invention, in which methane is produced.

FIG. 2 shows a schematic view of the second step of the depicted variant of the process according to the invention, which pertains to generation of methane from the hydrogen produced in the first step and separation of the produced methane.

The hydrogen ($H_2$) produced in the first step is fed to another bioreactor 2'. An aqueous solution of methanogenic bacteria is present in this bioreactor 2', which is separated from the gas space of bioreactor 2' by a membrane 3'. The membrane 3', as for the first step according to FIG. 1, consists of CLPE. Hydrogen ($H_2$) and carbon dioxide ($CO_2$) are fed to the methanogenic bacteria present in the aqueous solution. For this purpose, carbon dioxide (for example, originating from a gas liquefaction process) is converted to dry ice in the dry ice generator 1'.

The educts carbon dioxide ($CO_2$) and hydrogen ($H_2$) are fed to the bacterial solution under anaerobic conditions at a temperature of about 60° C. Appropriate nutrients 5' are also continuously added to the bacterial solution. Both the bacterial solution and the gases in the gas space of the bioreactor 2' are continuously circulated by pumps 4'.

In the method according to the invention, the methanogenic bacteria produce methane ($CH_4$) from the supplied hydrogen ($H_2$) and carbon dioxide ($CO_2$) by adjustment of appropriate environmental conditions and by the supply of nutrients 5'. The formed methane can diffuse through the membrane 3' made of CLPE into the gas space of bioreactor 2'. To prevent excess diffusion of hydrogen ($H_2$) and carbon dioxide ($CO_2$) into the gas space, the osmotic pressure of the two educts is increased on the gas side of membrane 3'.

Although the methanogenesis is conducted essentially under anaerobic conditions, occurrence or even enrichment of oxygen and/or oxygen radicals can occur intracellularly in the methanogenic bacteria. This intracellular oxygen, however, hampers methane production. It is therefore proposed, as an advantageous variant, to bind the intracellular oxygen of the methanogenic bacteria. For this purpose, as in the hydrogenesis algae, an appropriate binder can be added. Such a binder can act biochemically or chemically, in order to bind the intracellular oxygen. Appropriate binders include myoglobin, porphorin, hydrazine or terpenes.

The binder is preferably regenerated after absorbing the intracellular oxygen. The procedure can then be as described with reference to the hydrogenesis algae.

The gas mixture of carbon dioxide ($CO_2$), hydrogen ($H_2$) and methane ($CH_4$) can be removed from the gas space of the bioreactor 2'. The carbon dioxide ($CO_2$) is then initially separated in a cooling trap 7' and returned to circulation. Separation of the remaining components hydrogen ($H_2$) and methane ($CH_4$) occurs via a gas liquefaction 8' and downstream fractionation 9'. The separated hydrogen ($H_2$) is also returned to the process.

The product methane ($CH_4$) is left in high purity.

Figure 3:
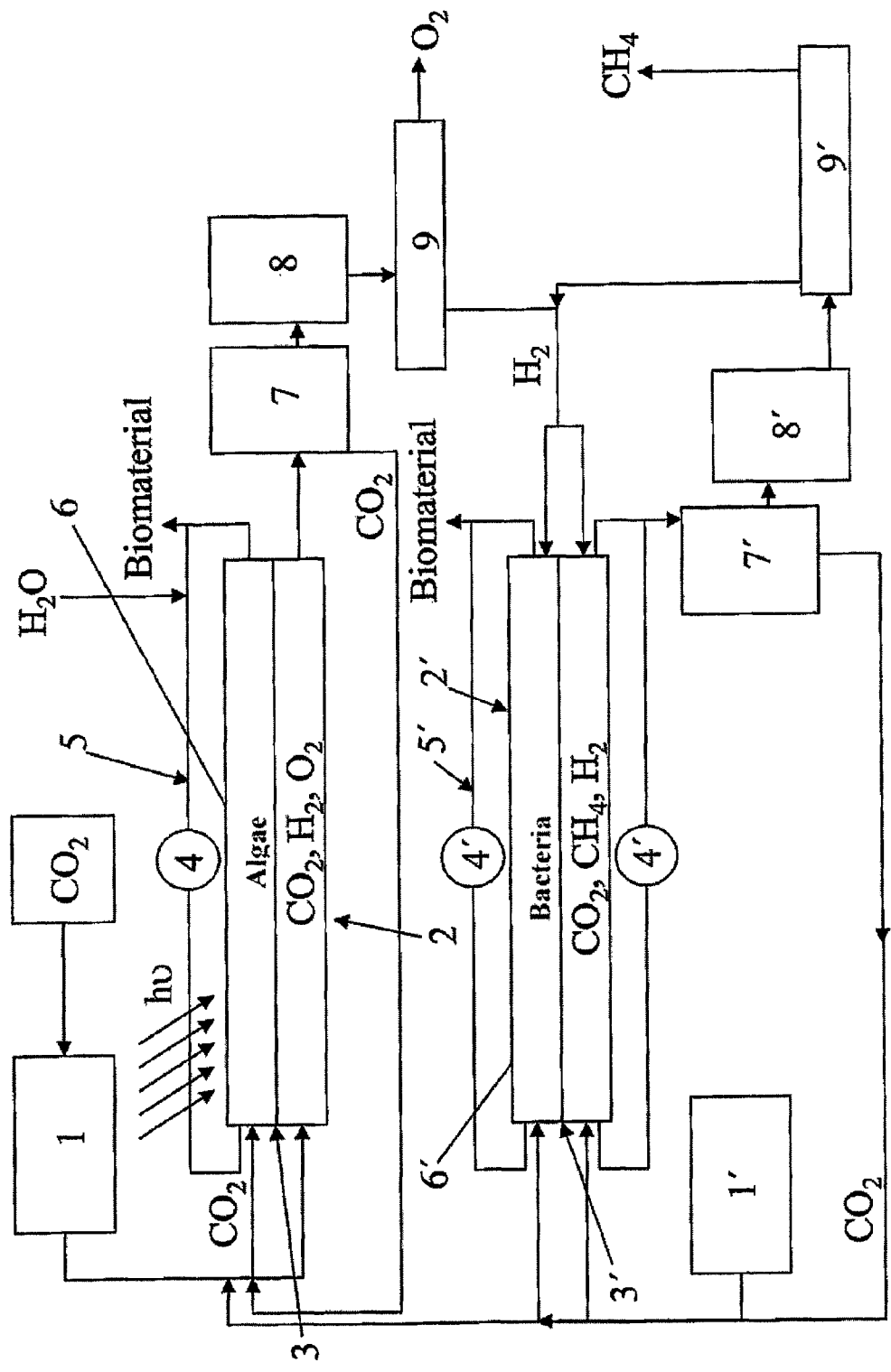
FIG. 3 shows a schematic view of the overall process according to the depicted variant and FIG. 4 shows a schematic view of a preferred membrane arrangement for separation of gaseous (intermediate) products from the algal or bacterial medium.

FIG. 3 shows a schematic view of the overall process. It is then clear how the hydrogen ($H_2$) produced in the first step is transferred for the second step and used. In addition, in the second step, obtained carbon dioxide ($CO_2$) is also returned to the first step. Excess biomaterial is also continuously formed in the second step through the continuous growth of the employed methanogenic bacteria, which is discharged from further membrane production in the biogas mixture.

The comments concerning FIGS. 1 and 2 are referred to for additional individual process steps, in order to avoid repetitions.

Figure 4:
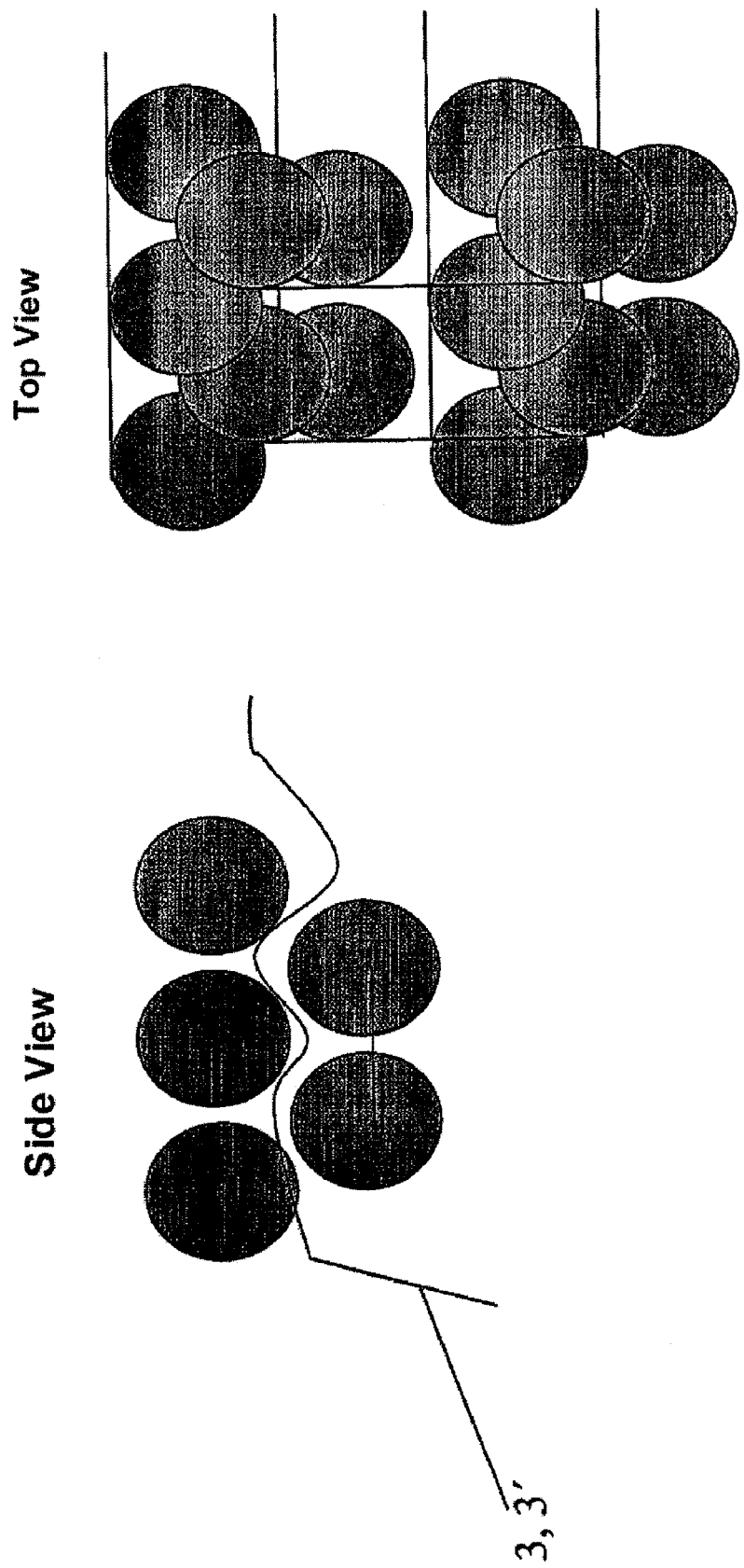

The following empirical reactions occur in the process according to the invention:

$1^{st}$ step (FIG. 1): $2H_2O \rightarrow 2H_2 + O_2$
$2^{nd}$ step (FIG. 2): $CO_2 + 4H_2 \rightarrow CH_4 + 2H_2O$
Overall (FIG. 3): $CO_2 + 2H_2O \rightarrow 2O_2 + CH_4$ FIG. 4 shows a schematic view of a preferred fastening of the membrane 3,3' used according to the invention. A membrane 3, 3' made of CLPE is then used in the method, both in hydrogen production by algae and in methane production by methanogenic bacteria, in order to permit transfer of gaseous products from an aqueous medium.

This figure shows, in a side view and in a top view, how the membrane 3, 3' made of CLPE is anchored in hexagonally closest spherical packing, in order to achieve the most reliable possible fastening of membrane 3, 3'.

This type of fastening of the membrane is then preferred in the method according to the invention, but not absolutely necessary for execution of the method.

Figure 5:
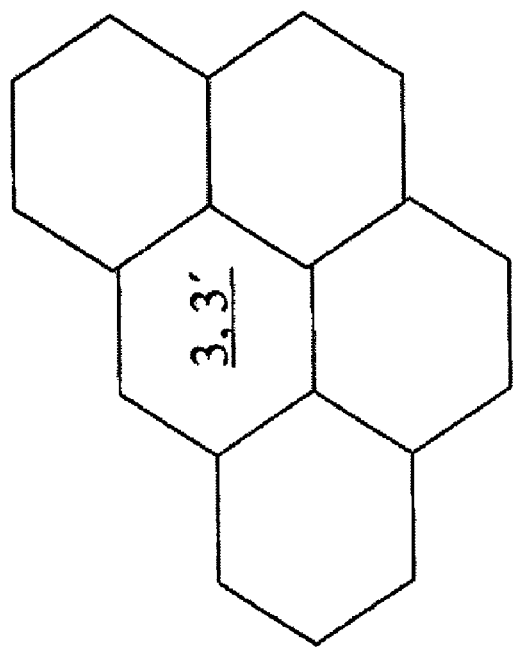
FIG. 5 shows a schematic view of two variants of multi-layer membranes that are preferably used for gas separation in the process according to the invention.
Figure 5:
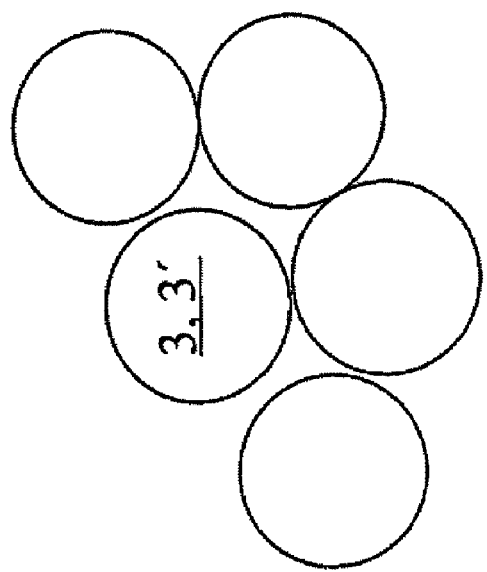

FIG. 5 shows a schematic view of two variants of multi-layer membranes, which are preferably used in the process according to the invention. The membranes 3, 3' consist of at least two layers and can have an inner layer made of PATBS. To increase the pressure resistance, the layers in membranes 3, 3' are welded to each other, at least in areas. A circular pattern is shown in FIG. 5 on the left. These circles can touch, or also be slightly spaced from each other. The different layers of membranes 3, 3' are welded to each other in a honeycomb pattern in FIG. 5 on the right, so that increased pressure stability is achieved.

During use of the preferred membranes, both in bioreactor 2 and in bioreactor 2', the pressure on the gas side of the membrane can be increased without its failure. As a result, the osmotic pressure of the carbon dioxide, in particular, can be further increased.

The membrane 3 in bioreactor 2 can be produced from black material. A larger heat excess occurs in the bioreactor 2 on this account, which can be advantageously used in the already described manner.

Finally, it is emphasized that the practical example of the process according to the invention described above explains the claimed teachings, but does not restrict them to the practical example.

The invention claimed:

1. A method for biological generation of methane ($CH_4$), the method having the steps:

Generation of hydrogen ($H_2$) and oxygen ($O_2$) from carbon dioxide ($CO_2$) and water ($H_2O$) by green algae under the influence of light (hydrogenesis), Separation of the gaseous intermediates hydrogen ($H_2$) and oxygen ($O_2$) from an algal medium via a membrane, Separation of the generated oxygen ($O_2$) from the generated hydrogen ($H_2$), Generation of methane ($CH_4$) from the generated hydrogen ($H_2$) and carbon dioxide ($CO_2$) by methanogenic bacteria (methanogenesis), Separation and optional liquefaction of the generated methane ($CH_4$).

2. The method according to claim 1, wherein the algae used to generate hydrogen ($H_2$) are prepared in an aqueous solution, to which appropriate nutrients are fed periodically or continuously, and/or the algae used to generate hydrogen ($H_2$) are Chlamydomonas reinhardtii.

3. The method according to claim 1, wherein the algae used for generation of hydrogen ($H_2$) are separated from the light source, by an essentially transparent disk, in which a disk, having a self-cleaning effect (lotus effect) on the side facing away from the light is used.

4. The method of claim 3, wherein the disk is produced by silane coating.

5. The method according to claim 1, wherein intracellular oxygen ($O_2$) is bonded in the algae, and bonded during or after the hydrogenesis step, in which the intracellular oxygen ($O_2$) is bonded by addition of at least one binder.

6. The method according to claim 5, wherein the intracellular oxygen ($O_2$) is biochemically bonded, in which myoglobin is added as binder and/or
porphorin is added as binder.

7. The method of claim 6, wherein the myoglobin and/or the prophorin is or are regenerated electrochemically and/or biochemically and/or physically after absorption of oxygen ($O_2$).

8. The method according to claim 5, wherein the intracellular oxygen ($O_2$) is chemically bonded, in which hydrazine and/or hydrazine salt is added as binder, and/or
a terpene and/or isoprene, is added as binder.

9. The method according to claim 8, wherein the hydrazine or salt thereof is iron-hydrazine, and the terpene is α-terpene.

10. The method of claim 5, wherein the binder or binders is or are regenerated after absorption of oxygen ($O_2$).

11. The method according to claim 1, wherein separation of the gaseous intermediates hydrogen ($H_2$) and oxygen ($O_2$) from the algal medium occurs via a porous membrane made of CLPE (cross-linked polyethylene), in which the membrane is fastened on both sides in hexagonal closest spherical packing, and/or in which a CLPE membrane with an inner layer of PATBS (poly (acrylamide-tert-butylsulfonic acid)) is used and/or a multilayer membrane is used, whose layers are welded to each other at least in areas, in a circular or honeycomb pattern, and/or in which the osmotic pressure of carbon dioxide ($CO_2$) is increased on the gas side of the membrane.

12. The method of claim 11, wherein the porous membrane is a black membrane.

13. The method according to claim 1, wherein separation of the generated oxygen ($O_2$) from the hydrogen ($H_2$) occurs by gas liquefaction, according to the Linde method.

14. The method according to claim 1, wherein excess hydrogen ($H_2$) and oxygen ($O_2$) are used to generate pure fresh water ($H_2O$), using the waste heat from the hydrogenesis step.

15. The method according to claim 1, wherein the methanogenic bacteria used to generate methane ($CH_4$) are prepared in an aqueous solution, and/or the methanogenic bacteria used to generate methane ($CH_4$) are a species or a mixture of species of Methanobacterium thermoautotropicum, Methanobacillus, Methanobacterium, Methanococcus, Methanosarcina and Methanothrix, and/or hydrogen ($H_2$) and carbon dioxide ($CO_2$) are fed to the methanogenic bacteria under anaerobic conditions and/or at a temperature of about 60° C., and/or intracellular oxygen ($O_2$) is bonded in the methanogenic bacteria, and bonded during the methanogenesis step.

16. The method according to claim 15, wherein separation of methane ($CH_4$) from the bacterial medium occurs via a a porous membrane made of CPLE (cross-linked polyethylene), in which the membrane is fastened on both sides in a hexagonal closest spherical packing, and/or in which a CLPE membrane with an inner layer of PATBS (poly (acrylamide-tert-butyl-sufonic acid)) is used, and/or in which a multilayer membrane is used, whose layers are welded to each other at least in areas, especially in a circular or honeycomb pattern, and/or in which the osmotic pressure of carbon dioxide ($CO_2$) is increased on the gas side of the membrane.

17. The method of claim 15, wherein appropriate nutrients are added periodically or continuously to the aqueous solution.

18. The method according to claim 1, wherein separation of methane ($CH_4$) from the bacterial medium occurs via a porous membrane made of CPLE (cross-linked polyethylene), in which the membrane is fastened on both sides in a hexagonal closest spherical packing, and/or in which a CLPE membrane with an inner layer of PATBS (poly (acrylamide-tert-butyl-sufonic acid)) is used, and/or in which a multilayer membrane is used, whose layers are welded to each other at least in areas, in a circular or honeycomb pattern, and/or in which the osmotic pressure of carbon dioxide ($CO_2$) is increased on the gas side of the membrane.

19. The method according to claim 1, wherein separation of the generated methane ($CH_4$) from hydrogen ($H_2$) occurs by gas liquefaction, according to the Linde method.

20. The method according to claim 1, wherein carbon dioxide ($CO_2$) fed to the algae and/or methanogenic bacteria is produced from dry ice, and/or carbon dioxide ($CO_2$) fed to the algae and/or methanogenic bacteria is prepared from carbon dioxide-enriched gas streams, from industrial and incineration processes, and/or the unconsumed or unconverted carbon dioxide ($CO_2$) is recovered, by means of a cooling trap, and returned to the process.

21. The method of claim 20, wherein the dry ice is produced from air liquefaction, according to the Linde method.

22. The method according to claim 1, wherein excess algal and/or bacterial material that forms is periodically or continuously removed and fed to a biogas process for additional methane production.

23. The method according to claim 1, wherein heat is taken off from the hydrogenesis step by a heat exchanger or heat pump in which heat is transferred between the hydrogenesis step and the methanogenesis step.

* * * * *

UNITED STATES PATENT AND TRADEMARK OFFICE
CERTIFICATE OF CORRECTION

| | | |
|---|---|---|
| PATENT NO. | : 8,323,938 B2 | Page 1 of 1 |
| APPLICATION NO. | : 12/518407 | |
| DATED | : December 4, 2012 | |
| INVENTOR(S) | : Salvetzki | |

It is certified that error appears in the above-identified patent and that said Letters Patent is hereby corrected as shown below:

Title page,
"(73) Assignee: Ralf Salvetzki, Wennigsen (DE)" should be deleted;
Item (57) ABSTRACT, "($H_2$)and oxygen ($O_2$)" should be --($H_2$) and oxygen ($O_2$)--.

In the Specification:

Column 1,
Line 65, "oxygen $0_2$" should read --oxygen $O_2$--.

Column 7,
Line 51, "hv" should read --hv--.

Signed and Sealed this
Twenty-third Day of July, 2013

Teresa Stanek Rea
*Acting Director of the United States Patent and Trademark Office*